US009302955B2

(12) United States Patent
Corradi et al.

(10) Patent No.: US 9,302,955 B2
(45) Date of Patent: Apr. 5, 2016

(54) SYSTEMS AND METHODS FOR SEPARATING XYLENE ISOMERS USING SELECTIVE ADSORPTION

(71) Applicant: UOP LLC, Des Plaines, IL (US)

(72) Inventors: Jason T. Corradi, Arlington Heights, IL (US); Gregory Werba, Arlington Heights, IL (US); Rajeswar Gattupalli, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 302 days.

(21) Appl. No.: 14/040,363

(22) Filed: Sep. 27, 2013

(65) Prior Publication Data

US 2015/0094508 A1    Apr. 2, 2015

(51) Int. Cl.
  *B01D 3/34*      (2006.01)
  *B01D 15/10*     (2006.01)
  *C07C 7/00*      (2006.01)
  *B01D 3/14*      (2006.01)
  *C07C 5/27*      (2006.01)
  *C07C 6/12*      (2006.01)
  *C07C 7/11*      (2006.01)

(52) U.S. Cl.
  CPC ............... *C07C 7/005* (2013.01); *B01D 3/143* (2013.01); *B01D 3/34* (2013.01); *B01D 15/10* (2013.01); *C07C 5/2732* (2013.01); *C07C 6/126* (2013.01); *C07C 7/11* (2013.01)

(58) Field of Classification Search
  None
  See application file for complete search history.

(56) References Cited

U.S. PATENT DOCUMENTS

| 3,558,732 | A | 1/1971  | Neuzil        |
| 3,663,638 | A | 5/1972  | Neuzil        |
| 3,700,744 | A | 10/1972 | Berger et al. |
| 3,813,452 | A | 5/1974  | Bieser        |
| 3,855,333 | A | 12/1974 | Neuzil        |
| 4,021,499 | A | 5/1977  | Bieser        |
| 4,255,607 | A | 3/1981  | Miyake et al. |

(Continued)

FOREIGN PATENT DOCUMENTS

| EP | 0003622 B1 | 1/1982 |
| EP | 1165471 A1 | 1/2002 |

(Continued)

OTHER PUBLICATIONS

PCT International Search Report for PCT/US2014/054008, mailing date Dec. 9, 2014, Applicant file reference H0038239.

(Continued)

*Primary Examiner* — Tam M Nguyen

(57) ABSTRACT

Methods and systems are provided for separating a selected xylene isomer. The method includes separating a feed stream including a plurality of aromatic hydrocarbons into a first stream including toluene and isomers of xylene, and a second stream including isomers of xylene. The method further includes separating the first stream into a third stream including toluene and a fourth stream including isomers of xylene. The method further includes combining the second stream and the third stream in an adsorptive separation unit including an adsorbent configured to adsorb the selected xylene isomer from the second stream. The third stream desorbs the selected xylene isomer to produce a fifth stream including the selected xylene isomer and toluene and a sixth stream including non-selected xylene isomers and toluene. Still further, the method includes separating the sixth stream into a seventh stream including the non-selected xylene isomers and the third stream including toluene.

12 Claims, 1 Drawing Sheet

(56) References Cited

U.S. PATENT DOCUMENTS

| | | |
|---|---|---|
| 4,326,092 A | 4/1982 | Neuzil |
| 4,368,347 A | 1/1983 | Carra et al. |
| 4,376,226 A | 3/1983 | Rosenfeld et al. |
| 4,381,419 A | 4/1983 | Wylie |
| 4,439,535 A | 3/1984 | Smolin et al. |
| 4,554,398 A | 11/1985 | Barthomeuf et al. |
| 4,615,994 A | 10/1986 | Smolin et al. |
| 4,899,017 A | 2/1990 | Yan |
| 5,453,560 A | 9/1995 | Kulprathipanja |
| 5,763,714 A | 6/1998 | Hickey et al. |
| 5,884,777 A | 3/1999 | Pan et al. |
| 5,900,523 A | 5/1999 | Kulprathipanja |
| 5,912,395 A | 6/1999 | Noe |
| 6,240,744 B1 | 6/2001 | Agrawal |
| 6,281,406 B1 | 8/2001 | Cain |
| 6,395,951 B1* | 5/2002 | Hamm ............. B01D 3/14 208/347 |
| 6,706,938 B2 | 3/2004 | Roeseler et al. |
| 6,841,714 B2 | 1/2005 | Leflaive et al. |
| 6,896,812 B1 | 5/2005 | Frey |
| 7,468,468 B2 | 12/2008 | Leflaive et al. |
| 7,622,034 B1 | 11/2009 | Thakkar |
| 7,687,674 B2 | 3/2010 | Wegerer |
| 7,728,187 B2 | 6/2010 | Kulprathipanja et al. |
| 7,915,471 B2 | 3/2011 | Leflaive et al. |
| 7,977,526 B2 | 7/2011 | Porter |
| 8,323,581 B2 | 12/2012 | Bresler et al. |
| 8,716,545 B1* | 5/2014 | Corradi ............. C07C 7/04 585/802 |
| 2006/0199989 A1* | 9/2006 | Frey ............. C07C 7/12 585/828 |
| 2008/0161626 A1* | 7/2008 | Wegerer ............. C07C 5/2702 585/805 |
| 2011/0245573 A1 | 10/2011 | Porter et al. |
| 2012/0004491 A1 | 1/2012 | Kulprathipanja et al. |
| 2012/0241384 A1 | 9/2012 | Porter |
| 2013/0153500 A1 | 6/2013 | Frey et al. |
| 2013/0153505 A1 | 6/2013 | Corradi et al. |
| 2013/0158330 A1 | 6/2013 | Corradi |
| 2013/0158333 A1* | 6/2013 | Corradi ............. C07C 7/12 585/822 |
| 2013/0158334 A1 | 6/2013 | Corradi |
| 2014/0171715 A1* | 6/2014 | Corradi ............. B01D 3/141 585/800 |

FOREIGN PATENT DOCUMENTS

| | | |
|---|---|---|
| WO | 2000058244 | 10/2000 |
| WO | 2013089863 A1 | 6/2013 |
| WO | 2013089900 A1 | 6/2013 |
| WO | 2013089901 A1 | 6/2013 |
| WO | 2013089902 A1 | 6/2013 |
| WO | 2013089920 A2 | 6/2013 |
| WO | 2013089921 A1 | 6/2013 |
| WO | 2013089922 A1 | 6/2013 |
| WO | 2013089923 A1 | 6/2013 |

OTHER PUBLICATIONS

Rasouli, et al., "Effect of Nanocrystalline Zeolite Na-Y on Meta-Xylene Separation," Microporous and Mesoporous Materials (2012), 152, 141-147.

Rasouli, et al., "Influence of Monovalent Cations Ion-Exchange on Zeolite ZSM-5 in Separation of Para-Xylene from Xylene Mixture," Microporous and Mesoporous Materials (2012), 150, 47-54.

Bergeot, et al., "Intensification of Paraxylene Production Using a Simulated Moving Bed Reactor," Oil & Gas Science and Technology (2010), 65(5), 721-733.

Guo, et al., "Separation of P-Xylene from C8 Aromatics on Binder-Free Hydrophobic Adsorbent of MFI Zeolite. I. Studies on Static Equilibrium," Microporous and Mesoporous Materials (2000), 39(1-2), 149-161.

Chiang, et al., "Chromatographic Separation of Xylenes with Silicalite," Int. Conf. Fundam. Adsorpt., 3rd (1991), Meeting Date 1989, 199-210, Editor(s): Mersmann, Alfons B.; Scholl, Stephan E.; Publisher: AIChE, New York, N.Y.

* cited by examiner

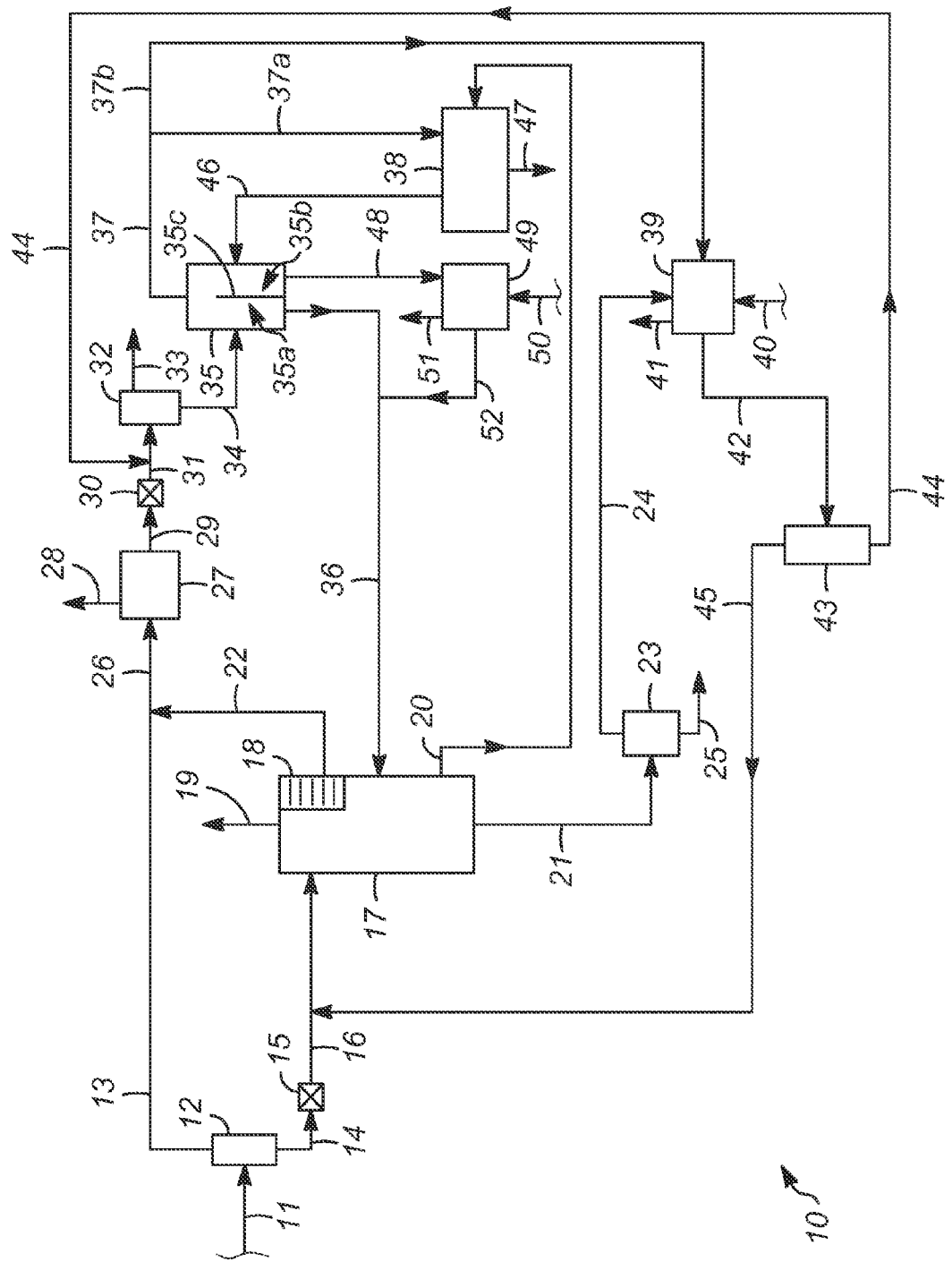

SYSTEMS AND METHODS FOR SEPARATING XYLENE ISOMERS USING SELECTIVE ADSORPTION

TECHNICAL FIELD

The present disclosure generally relates to systems and methods for separating aromatic hydrocarbons, and more particularly relates to systems and methods for separating isomers of xylene using selective adsorption.

BACKGROUND

Xylene isomers are important intermediates in chemical syntheses, and specific xylene isomers are desired for different processes. Paraxylene is a feedstock for terephthalic acid, and terephthalic acid is used in the manufacture of synthetic fibers and resins. Metaxylene is used in the manufacture of certain plasticizers, azo dyes, and wood preservatives. Orthoxylene is a feedstock for phthalic anhydride production, and phthalic anhydride is used in the manufacture of certain plasticizers, dyes, and pharmaceutical products.

Xylene isomers typically are separated from mixed xylene streams by using an adsorbent selective to the desired isomer. The desired isomer is adsorbed, and the remaining isomers are discharged in a mixed raffinate stream. A desorbent is then used to desorb the desired xylene isomer, and the desorbent and desired xylene isomer are collected and separated by distillation (also referred to as fractionation). The desorbents are typically referred to as either heavy or light, where a heavy desorbent has a higher molecular weight and a higher boiling point than xylene and a light desorbent has a lower molecular weight and a lower boiling point than xylene. Xylene isomer recovery systems with heavy desorbents tend to use less energy than systems with light desorbents because the desorbent does not need to be repeatedly evaporated and lifted in the fractionation step. However, heavy desorbent systems require stringent feed purity to control the accumulation of undesired compounds in the recycled desorbent. The undesired compounds are impurities that reduce the desorbent effectiveness and product purity. Additional equipment is needed to maintain the heavy desorbent purity during the desorbent recycling process. The distillation columns in heavy desorbent systems have higher reboiler temperatures, which leads to higher operating pressures. These higher operating pressures require higher pressure ratings for the equipment involved, which increase the equipment capital costs and maintenance expenses.

A light desorbent system allows a relaxed feed specification relative to a heavy desorbent system. This helps to offset the increased energy costs associated with recovering light desorbent as a distillation column overhead stream. The light desorbent systems also provide substantial savings in the total equipment count for xylene recovery systems, because the additional equipment for desorbent storage and recovery is not needed. The light desorbent xylene recovery systems also have lower distillation column operating pressures, so thinner shell thicknesses and lower pressure ratings can be used to further reduce capital costs for installing new systems. Toluene is one example of a light desorbent that can be used, and toluene is less expensive than many of the heavy desorbents available.

As such, in the prior art, a trade-off exists between systems that use heavy desorbents and systems that use light desorbents. In situations where the feed specification is not able to be tightly controlled, it may be desirable to use a light desorbent system as opposed to a heavy desorbent system for the reasons discussed above. However, the prior art fails to disclose any systems that address the undesirable increase in energy use associated with such light desorbent systems.

Accordingly, it is desirable to develop methods and systems for producing selected xylene isomers from mixed xylene streams using light desorbents in a manner that reduces overall energy consumption. Furthermore, other desirable features and characteristics of the present embodiment will become apparent from the subsequent detailed description and the appended claims, taken in conjunction with the accompanying drawings and this background.

BRIEF SUMMARY

Methods and systems are provided for separating a selected xylene isomer. In one exemplary embodiment, a method for separating a selected xylene isomer includes the steps of separating a feed stream including a plurality of aromatic hydrocarbons into a first stream including toluene and isomers of xylene, and a second stream including isomers of xylene. The method further includes separating, in a first zone of a multi-zone separation apparatus, the first stream into a third stream including toluene and a fourth stream including isomers of xylene. The method further includes combining the second stream and the third stream in an adsorptive separation unit including an adsorbent configured to adsorb the selected xylene isomer from the second stream. The third stream desorbs the selected xylene isomer from the adsorbent to produce a fifth stream including the selected xylene isomer and toluene and a sixth stream including non-selected xylene isomers and toluene. Still further, the method includes separating, in a second zone of the multi-zone separation apparatus, the sixth stream into a seventh stream including the non-selected xylene isomers and the third stream including toluene.

In another exemplary embodiment, a system for separating a selected xylene isomer includes a first hydrocarbon separation apparatus configured to separate a feed stream including a plurality of aromatic hydrocarbons into a first stream including toluene and isomers of xylene, and a second stream including isomers of xylene. The system further includes a multi-zone separation apparatus including a first separation zone configured to separate the first stream into a third stream including toluene and a fourth stream including isomers of xylene. Still further, the system includes an adsorptive separation unit including an adsorbent configured to adsorb the selected xylene isomer from the second stream. The third stream desorbs the selected xylene isomer from the adsorbent to produce a fifth stream including the selected xylene isomer and toluene and a sixth stream including non-selected xylene isomers and toluene. Additionally, the multi-zone separation apparatus includes a second separation zone configured to separate the sixth stream into a seventh stream including the non-selected xylene isomers and the third stream including toluene.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWING

The present embodiments will hereinafter be described in conjunction with the following drawing FIGURE, wherein like numerals denote like elements, and wherein:

FIG. 1 is a process flow diagram illustrating a method implemented on a xylene isomer separation system in accordance with various embodiments of the present disclosure.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The various embodiments described herein relate to systems and methods for separating a selected xylene isomer from a mixed xylene feedstock using adsorptive separation with a light desorbent. In the disclosed systems, certain separation apparatus, in particular distillation columns, are combined in a novel manner to reduce the overall equipment count needed to implement the system, thereby lowering the overall energy costs, which, as noted above, tend to be higher in light desorbent systems. As such, the present disclosure provides separation systems and methods that improve over the prior art by allowing for a relaxed-specification (i.e., less tightly controlled specification) feed stock, while at the same time reducing overall energy costs.

Reference is now made to FIG. 1, which provides a process flow diagram illustrating a method implemented on a xylene isomer separation system 10 in accordance with various embodiments of the present disclosure. As shown therein, a feed stream 11 is provided to system 10. Suitable feed streams 11 for separating a selected xylene isomer are available from many sources. For example, a fluid catalytic cracking (FCC) unit and fractionator, when run in high severity mode, can produce a fraction with hydrocarbons having 7 to 10 carbon atoms (C7-C10), where about 60 mass percent of the hydrocarbons are aromatic. Certain coal liquefaction processes produce hydrocarbon streams rich in aromatic compounds, and these hydrocarbon streams are suitable for use as the feed stream 11. Other possible sources include various petroleum refining processes, thermal or catalytic cracking of hydrocarbons, or petrochemical conversion processes, including hydrocarbon streams processed in a reformer using a catalyst designed to produce aromatic compounds, such as reformed naphthas.

In one particular embodiment, the feed stream 11 is a naphtha stream. Naphtha feedstocks include aromatics, paraffins, and naphthenes, and may include small amounts of olefins. Feedstocks which may be utilized include straight-run naphthas, natural gasoline, synthetic naphthas, thermal gasoline, catalytically cracked gasoline, and in particular reformed naphthas. The feedstock may be encompassed by a full-range naphtha as defined by boiling points, or from about 0° to about 230° C., although naphthas having a greater percentage (such as greater than about 50%, greater than about 70%, etc.) of aromatic hydrocarbons are preferred.

As shown in FIG. 1, the feed stream 11, particularly in embodiments where the feed stream 11 is a reformed naptha stream, is fed to a reformate splitter distillation column 12. The reformate splitter distillation column 12 functions to separate or "split" by distilling the feed stream 11 into a lower boiling stream as an overhead stream 13 and a higher boiling stream as a bottom stream 14. The reformate splitter distillation column may be configured such that, for example, the overhead stream 13 may include primarily (such as greater than about 80%, greater than about 90%, or greater than about 95%) hydrocarbon molecules having seven or fewer carbon atoms (C7-). The bottom stream 14 may thus include primarily (such as greater than about 80%, greater than about 90%, or greater than about 95%) hydrocarbon molecules having eight or more carbon atoms (C8+).

The bottom stream 14 may thereafter be passed to a clay treater 15 for the removal of any alkylates and olefins that may be present in the stream 14, as is known in the art. The clay treater 15 may be configured in any known manner suitable for this purpose. Stream 16 leaving the clay treater 15 may thus include primarily (such as greater than about 80%, greater than about 90%, or greater than about 95%) C8+ hydrocarbons with alkylate and olefin compounds substantially (such as greater than about 90%) removed therefrom.

C8+ hydrocarbons stream 16 is thereafter passed to a "stripper" distillation column 17 for separating the stream 16 into various fractions. The different fractions (such as C7-, C8, and C9+) are separated based on the relative boiling points of the compounds present. As shown in FIG. 1, stripper distillation column 17 includes a "stabilizer" distillation column associated therewith. Stabilizer distillation column 18, in one embodiment, is integrated within an overhead portion of the stripper distillation column 17, as illustrated. By integrating the stabilizer distillation column 18 within the stripper distillation column 19, capital costs can be reduced by eliminating a dedicated stabilizer vessel. In this embodiment, vessel partitions provide isolation from the main stripper tray section so that a portion of the overhead liquid can be stabilized. In another embodiment, however, the stabilizer 18 may be a separate unit. Regardless of the particular configuration, the stripper distillation column 17 produces an overhead stream 19 that may include primarily (such as greater than about 80%, greater than about 90%, or greater than about 95%) hydrocarbon molecules having four or fewer carbon atoms (C4-). The column 17 further produces a mixed xylene stream 20 as a "side draw" product that may include primarily (such as greater than about 80%, greater than about 90%, or greater than about 95%) C8+ hydrocarbons. Still further, the column 17 produces, as a bottom stream 21, a stream that primarily (such as greater than about 80%, greater than about 90%, or greater than about 95%) includes hydrocarbon molecules having nine or more carbon atoms (C9+). The stabilizer 18, which as noted above is associated with an overhead portion of the stripper distillation column 17, receives a portion of the hydrocarbons in the overhead portion of the stripper distillation column 17 and produces a liquid product stream 22 including primarily (such as greater than about 80%, greater than about 90%, or greater than about 95%) hydrocarbons having between 5 and 7 carbons atoms (C5-C7) and a gas product stream, which includes primarily (such as greater than about 80%, greater than about 90%, or greater than about 95%) C4-hydrocarbons and is joined with the overhead stream 19 in the stripper distillation column.

C9+ stream 21 is thereafter passed to a further "heavy aromatics" distillation column 23 for further separation of the stream 21. The heavy aromatics distillation column 23 produces as an overhead stream 24 a stream that includes primarily (such as greater than about 80%, greater than about 90%, or greater than about 95%) hydrocarbons having either nine or ten carbon atoms (C9-C10). The heavy aromatics distillation column 23 further produces a bottom stream 25 that includes primarily (such as greater than about 80%, greater than about 90%, or greater than about 95%) hydrocarbons having eleven or more carbon atoms (C11+). The overhead stream 24 is passed to a transalkylation unit (unit 39 in FIG. 1), as will be described in greater detail below, for producing additional C8 aromatic hydrocarbons. The bottom stream 25 is removed from the system 10 and may be used as fuel, as input material for other processes, or otherwise utilized. As an additional matter, C4- stream 19 from the stripper distillation column 17 (and also from the stabilizer distillation column 18) is also removed from the system 10 and may be used as fuel, as input material for other processes, or otherwise utilized.

C5-C7 stream 22 may be joined with C7– reformate splitter distillation column overhead stream 13. This combined stream 26, including primarily (such as greater than about 80%, greater than about 90%, or greater than about 95%) C7– hydrocarbons, is thereafter passed to an extractive distillation process unit 27 for removing non-aromatic compounds from the stream 26. In one particular embodiment, extractive distillation process unit 27 may employ a sulfolane solvent to separate aromatic compounds from non-aromatic compounds, as is known in the art. Other extraction methods, such as liquid-liquid solvent extraction are also known in the art and practiced for separation of non-aromatic compounds from aromatic compounds, and their use in place of or in addition to unit 27 is within the scope of the present disclosure. Extractive distillation unit 27 produces a first stream 28 that includes primarily (such as greater than about 80%, greater than about 90%, or greater than about 95%) C7– non-aromatic hydrocarbons and a second stream 29 that includes primarily (such as greater than about 80%, greater than about 90%, or greater than about 95%) benzene and toluene. The second stream 29 may further be passed to a clay treater 30 for increasing the purity of the aromatic compounds in such stream, for example by removing any alkylates or olefins that may be present therein in a manner as described above with regard to clay treater 15, thus producing a treated benzene and toluene stream 31.

The treated benzene and toluene stream 31 is thereafter passed to a further distillation column 32 for the separation of the benzene from the toluene in the stream 31. The benzene, having a lower boiling point than toluene, is removed from column 32 as an overhead product 33, and the toluene, having a higher boiling point than benzene, is removed from column 32 as a bottom product 34. Bottom product 34, which includes primarily (such as greater than about 40%, greater than about 60%, or greater than about 70%) toluene, but may also include some percentage of heavier aromatic hydrocarbons such as various xylene isomers, is thereafter passed to a multi-zone separation apparatus, such as a split shell distillation column 35, for further purification of the toluene. Split shell distillation column 35 includes a first zone or "side" 35a and a second zone or "side" 35b, which are separated from one another in the mid and lower portions of the column by baffle 35c, but which share a common upper (overhead) portion, as shown in FIG. 1. Toluene stream 34 is provided to the first side 35a, wherein any heavier aromatic compounds are removed as a bottom product of the first side 35a in stream 36 (which may then be recycled back to the stripper distillation column 17 as shown in FIG. 1), and wherein the purified toluene is removed as an overhead product in stream 37.

The purified toluene stream 37 is thereafter provided as a "light" desorbent (stream 37a) for the separation of selected xylene isomers in adsorptive separation unit 38 and also as a feed material (stream 37b) for the previously-alluded-to transalkylation unit 39. First, regarding the transalkylation unit 39, the toluene stream 37b is provided to the unit 39 wherein it is reacted with the C9-C10 stream 24 from the heavy aromatics distillation column 23. As is known in the art, transalkylation is a process that converts toluene and heavier (i.e., C9-C10) aromatics into mixed xylenes. Hydrogen gas is provided as a further feed material for the transalkylation reactions via stream 40. Transalkylation processes may employ, for example, silica-alumina and zeolites such as dealuminated mordenite, ultra stable Y-zeolite (USY), and ZSM-12 as catalysts for the transalkylation reactions. During the process of xylene production, a number of reactions such as disproportionation, transalkylation, and dealkylation take place. The methyl groups are shifted from one phenyl group to another via disproportionation and transalkylation to produce mixed xylenes. During dealkylation, the ethyl, propyl, and butyl groups attached to phenyl groups are removed to produce benzene and toluene. The transalkylation unit 39 produces a byproduct stream 41 that includes hydrocarbon gasses such as butane, propane, etc., and a stream 42 that includes primarily (such as greater than about 40%, greater than about 60%, or greater than about 70%) xylenes and toluene.

The xylene/toluene stream 42 is thereafter passed to a further stripper distillation column 43 for purifying the xylene/toluene stream 42, for example, by separating out any lighter aromatics (benzene, toluene) that may be present in the xylene/toluene stream 42. Any benzene or toluene present is removed from the stripper distillation column 43 via stream 44, which is then recycled back to join with benzene and toluene stream 31 prior to its entry into the distillation column 32. The xylene product, which is removed from the distillation column 43 via stream 45, is then recycled back to join with hydrocarbons stream 16 prior to its entry into the stripper distillation column 17. (Note that although illustrated in "reverse" for ease of illustration, stream 44 is the "overhead" stream and stream 45 is the "bottoms" stream of the distillation column 43.)

Turning now to the adsorptive separation unit 38, as shown in FIG. 1, stream 20, which as noted above is the mixed xylene stream removed as a side-draw from the stripper distillation column 17, provides the xylene feed product to the adsorptive separation unit 38. The mixed xylene stream 20 is introduced to the unit 38 to absorb a selected xylene isomer. The selected xylene isomer is paraxylene in many embodiments, but the selected xylene isomer may also be metaxylene in other embodiments. The separation unit 38 includes a selective adsorbent that preferentially adsorbs the selected xylene isomer over the other xylene isomers. In an exemplary embodiment, the selective adsorbent may be crystalline aluminosilicate, such as type X or type Y crystalline aluminosilicate zeolites. The selective adsorbent contains exchangeable cationic sites with one or more metal cations, where the metal cations can be one or more of lithium, potassium, beryllium, magnesium, calcium, strontium, barium, nickel, copper, silver, manganese, and cadmium. Adsorption conditions vary, but typically range from about 35° C. to about 200° C. (about 100° F. to about 400° F.) and from about 100 kPa to about 3,500 kPa (about 14 PSIG to about 500 PSIG).

The mixed xylene stream 20 is separated into a mixed raffinate stream 46 and an extract stream in the adsorptive separation unit 38. An extract column (not shown) is used to separate the toluene desorbent from the selected xylene isomer (such as paraxylene) in the mixed extract stream, thereby producing paraxylene product stream 47. The selective adsorbent preferentially adsorbs the selected xylene isomer, and the remaining raffinate xylene isomers are discharged with excess desorbent in the mixed raffinate stream 46. Desorbent is charged into the unit 38 by the toluene "light" desorbent stream 37a to desorb the selected xylene isomer. The desorbent is then separated from the selected isomer by distillation that occurs within the unit 38, and the selected xylene isomer is discharged as product stream 47, which is removed from the system 10 as the selected xylene product. Several different embodiments of the adsorptive separation unit 38 are possible, such as a single bed operated in batch fashion, where the mixed raffinate stream 46 is collected before the desired xylene isomer is desorbed, and the extract stream is collected after desorbing. In another embodiment, a plurality of adsorbent beds are used, and the introduction point of the mixed xylene stream 20 and the desorbent stream 37a are gradually moved through the different adsorbent beds. The discharge points of the extract stream and the mixed raffinate stream 46 are also gradually moved through the different adsorbent beds, so each individual adsorbent bed is used in a semi-batch mode and the combination simulates a continuous operation. As noted above, the desorbent has a lower molecular weight than xylene, and a desorbent boiling point lower than the selected xylene isomer boiling point or the raffinate xylene isomer(s) boiling point.

The mixed raffinate stream 46 produced from adsorptive separation unit 38 is thereafter passed to the second side 35b of the split shell distillation column 35. In the second side 35b, toluene desorbent in the mixed raffinate stream 46 is separated by boiling point distillation from the non-selected xylene isomers. The toluene, as noted above, is removed from the split-shell distillation column 35 in the combined overhead region via stream 37 for recycling back to streams 37a and 37b, and the non-selected xylene isomers are removed as a bottom product from the second side 35b via stream 48. The use of the split-shell configuration for the distillation column 35 saves capital cost as compared to a system that uses two separate distillation columns. As the overhead product for the distillation occurring in side 35a and side 35b is the same (i.e., toluene), comingling the overhead product while maintaining separate mid and bottom regions allows for two separate distillation processes to be integrated into a single distillation column, thereby requiring only one distillation column and common overhead system equipment.

The non-selected xylene isomer stream 48 is thereafter passed to an isomerization unit 49 wherein the raffinate xylene isomers, which are the xylene isomers other than the selected xylene isomer, are isomerized to produce more of the selected xylene isomer. The selected xylene isomer was removed in the adsorptive separation unit 38, and the removal of one isomer shifts the isomer composition away from equilibrium. As such, the selected xylene isomer, which is the isomer primarily absent from the stream 48, is produced in the isomerization unit 49 to bring the mixture closer to an equilibrium ratio. The equilibrium ratio is about 20 to about 25 percent orthoxylene, about 20 to about 30 percent paraxylene, and about 50 to about 60 percent metaxylene at about 250° C., and this equilibrium ratio varies with temperature and other conditions.

In an exemplary embodiment, the isomerization unit 49 includes an isomerization catalyst, and operates at suitable isomerization conditions. Suitable isomerization conditions include a temperature from about 100° C. to about 500° C. (about 200° F. to about 900° F.), or from about 200° C. to about 400° C. (about 400° F. to about 800° F.), and a pressure from about 500 kPa to about 5,000 kPa (about 70 PSIA to about 700 PSIA). The isomerization unit includes a sufficient volume of isomerization catalyst to provide a liquid hourly space velocity, with respect to the stream 48, from about 0.5 to about 50 hr$^{-1}$, or from about 0.5 to about 20 hr$^{-1}$. Hydrogen may be provided to the isomerization unit via stream 50 at up to about 15 moles of hydrogen per mole of xylene, but in some embodiments hydrogen is essentially absent from the isomerization unit 49. The isomerization unit 49 may include one, two, or more reactors, where suitable means are employed to ensure a suitable isomerization temperature at the entrance to each reactor. The xylenes are contacted with the isomerization catalyst in any suitable manner, including upward flow, downward flow, or radial flow.

In one embodiment, the isomerization catalyst includes a zeolitic aluminosilicate with a Si:Al$_2$ ratio greater than about 10/1, or greater than about 20/1 in some embodiments, and a pore diameter of about 5 to about 8 angstroms. Some examples of suitable zeolites include, but are not limited to, MFI, MEL, EUO, FER, MFS, MTT, MTW, TON, MOR, and FAU, and gallium may be present as a component of the crystal structure. In some embodiments, the Si:Ga$_2$ mole ratio is less than 500/1, or less than 100/1 in other embodiments. The proportion of zeolite in the catalyst is generally from about 1 to about 99 weight percent, or from about 25 to about 75 weight percent. In some embodiments, the isomerization catalyst includes about 0.01 to about 2 weight percent of one or more of ruthenium (Ru), rhodium (Rh), palladium (Pd), osmium (Os), Iridium (Ir), and platinum (Pt), but in other embodiments the isomerization catalyst is substantially absent of any metallic compound, where substantial absence is less than about 0.01 weight percent. The balance of the isomerization catalyst is an inorganic oxide binder, such as alumina, and a wide variety of catalyst shapes can be used, including spherical or cylindrical.

An isomerized xylene stream 52 exits the isomerization unit 49 and returns to the stripper distillation column 17 after joining with first side bottom product stream 36. A byproduct stream 51 that include light gasses such as butane, propane, etc., is also removed from the isomerization unit 49. The isomerized xylene stream 52 includes more of the selected xylene isomers than in the isomerization raffinate stream 46, so more of the selected xylene isomer is available for recovery. In this manner, the total amount of the selected xylene isomer recovered may exceed the equilibrium value.

As such, described herein are various exemplary systems and methods for separating a selected xylene isomer from a mixed xylene feedstock using adsorptive separation with a light desorbent. In the disclosed systems, certain separation apparatus, for example distillation columns 17 and 18, and 35a and 35b (as split-shell column 35), are combined in a novel manner to reduce the overall equipment count needed to implement the system, thereby lowering the overall production costs, which, as noted above, tend to be higher in light desorbent systems. As such, the present disclosure provides separation systems and methods that improve over the prior art by allowing for a relaxed-specification (i.e., less tightly controlled specification) feed stock typical of light desorbent systems (which results in energy savings), while at the same time reducing overall capital costs as compared to systems known in the prior art.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described in an exemplary embodiment without departing from the scope, as set forth in the appended claims.

The invention claimed is:

1. A method for separating a selected xylene isomer comprising the steps of:

separating a feed stream comprising a plurality of aromatic hydrocarbons into a first stream comprising toluene and isomers of xylene, and a second stream comprising isomers of xylene;

separating, in a first zone of a multi-zone separation apparatus, the first stream into a third stream comprising toluene and a fourth stream comprising isomers of xylene;

combining the second stream and the third stream in an adsorptive separation unit comprising an adsorbent configured to adsorb the selected xylene isomer from the second stream, wherein the third stream desorbs the selected xylene isomer from the adsorbent to produce a fifth stream comprising the selected xylene isomer and toluene and a sixth stream comprising non-selected xylene isomers and toluene; and separating, in a second zone of the multi-zone separation apparatus, the sixth stream into a seventh stream comprising the non-selected xylene isomers and the third stream comprising toluene.

2. The method of claim 1, wherein separating the feed stream comprises separating a reformed naphtha stream.

3. The method of claim 1, wherein separating the feed stream into the first stream and the second stream comprises performing a first separation process in a splitter distillation column to form an overhead product and a bottom product therefrom, and performing a second separation process in a stripper distillation column comprising a stabilizer column integrated into the stripper distillation column, wherein performing the second separation process comprises producing a stabilizer product from the stabilizer and a side-draw product from the stripper distillation column, wherein the stabilizer product and the overhead product are combined to form the first stream and the side-draw product form the second stream.

4. The method of claim 1, wherein separating the feed stream further comprises forming an eighth stream comprising C9+ hydrocarbons.

5. The method of claim 4, further comprising transalkylating the eighth stream to form a stream comprising additional isomers of xylene.

6. The method of claim 5, wherein transalkylating the eighth stream comprises combining the eighth stream with a portion of the third stream in a transalkylation reactor.

7. The method of claim 6, further comprising combining the stream comprising additional isomers with the second stream.

8. The method of claim 1, further comprising isomerizing the seventh stream comprising the non-selected xylene isomers to form a ninth stream comprising both the selected xylene isomer and the non-selected xylene isomers.

9. The method of claim 8, further comprising combining the ninth stream with the second stream.

10. The method of claim 1, wherein adsorbing the selected xylene isomer comprises adsorbing para-xylene.

11. The method of claim 1, wherein adsorbing the selected xylene isomer comprises adsorbing para-xylene.

12. A method for separating a selected xylene isomer comprising the steps of:

separating a feed stream comprising a plurality of aromatic hydrocarbons into a first stream comprising toluene and isomers of xylene, and a second stream comprising isomers of xylene, wherein separating the feed stream into the first stream and the second stream comprises performing a first separation process in a splitter distillation column to form an overhead product and a bottom product therefrom, and performing a second separation process in a stripper distillation column comprising a stabilizer column integrated into the stripper distillation column, wherein performing the second separation process comprises producing a stabilizer product from the stabilizer and a side-draw product from the stripper distillation column, wherein the stabilizer product and the overhead product are combined to form the first stream and the side-draw product form the second stream;

separating, in a first zone of a multi-zone separation apparatus, the first stream into a third stream comprising toluene and a fourth stream comprising isomers of xylene;

combining the second stream and the third stream in an adsorptive separation unit comprising an adsorbent configured to adsorb the selected xylene isomer from the second stream, wherein the third stream desorbs the selected xylene isomer from the adsorbent to produce a fifth stream comprising the selected xylene isomer and toluene and a sixth stream comprising non-selected xylene isomers and toluene;

separating, in a second zone of the multi-zone separation apparatus, the sixth stream into a seventh stream comprising the non-selected xylene isomers and the third stream comprising toluene; and isomerizing the seventh stream comprising the non-selected xylene isomers to form an eighth stream comprising both the selected xylene isomer and the non-selected xylene isomers.

* * * * *